(12) United States Patent
Uchida et al.

(10) Patent No.: US 10,064,588 B2
(45) Date of Patent: Sep. 4, 2018

(54) MOBILE X-RAY DIAGNOSTIC APPARATUS

(71) Applicant: Toshiba Medical Systems Corporation, Otawara-shi (JP)

(72) Inventors: Naoki Uchida, Utsunomiya (JP); Makoto Ishii, Nasushiobara (JP); Tsutomu Ichikawa, Yokohama (JP); Noriaki Baba, Minato (JP); Kenji Ido, Yokohama (JP); Masahiko Kitayama, Suginami (JP); Kousuke Yoneta, Nakano (JP); Izumi Fukunaga, Setagaya (JP)

(73) Assignee: Toshiba Madical Systems Corporation, Otawara-shi (JP)

( * ) Notice: Subject to any disclaimer, the term of this patent is extended or adjusted under 35 U.S.C. 154(b) by 0 days.

(21) Appl. No.: 14/754,936

(22) Filed: Jun. 30, 2015

(65) Prior Publication Data
US 2016/0000390 A1  Jan. 7, 2016

(30) Foreign Application Priority Data

Jul. 7, 2014 (JP) .................................. 2014-139909

(51) Int. Cl.
*A61B 6/00* (2006.01)
*A61B 6/06* (2006.01)

(52) U.S. Cl.
CPC .............. *A61B 6/4405* (2013.01); *A61B 6/06* (2013.01); *A61B 6/4283* (2013.01); *A61B 6/4476* (2013.01); *A61B 6/467* (2013.01)

(58) Field of Classification Search
CPC ....... A61B 6/4405; A61B 6/06; A61B 6/4283; A61B 6/4476; A61B 6/467
USPC ......................................... 378/193, 197, 198
See application file for complete search history.

(56) References Cited

U.S. PATENT DOCUMENTS

2010/0329426 A1* 12/2010 Oda ..................... A61B 6/4283
378/98.2
2011/0123001 A1* 5/2011 Kopcienski .......... A61B 6/4405
378/198

FOREIGN PATENT DOCUMENTS

| JP | 5-9512 U   | 2/1993  |
| JP | 2002-45353 | 2/2002  |
| JP | 2004-350833| 12/2004 |

* cited by examiner

*Primary Examiner* — Nicole Ippolito
*Assistant Examiner* — Hanway Chang
(74) *Attorney, Agent, or Firm* — Oblon, McClelland, Maier & Neustadt, L.L.P.

(57) ABSTRACT

A mobile X-ray-diagnostic apparatus of an embodiment includes an X-ray generator, an arm, a main body, a support column, and at least two input equipment. The X-ray generator generates X-rays. The arm holds the X-ray generator at one end. The main body includes wheels. The support column is turnably supported about a vertical direction as an axis, and supports another end of the arm. The at least two input equipment are arranged on the support column such that heights in the vertical direction differ from each other, and controls driving of the main body.

13 Claims, 14 Drawing Sheets

FIG.1
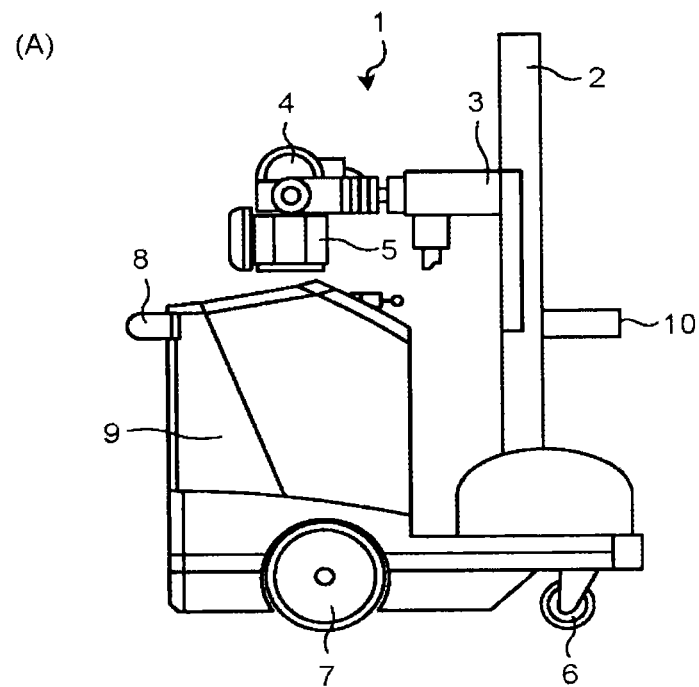
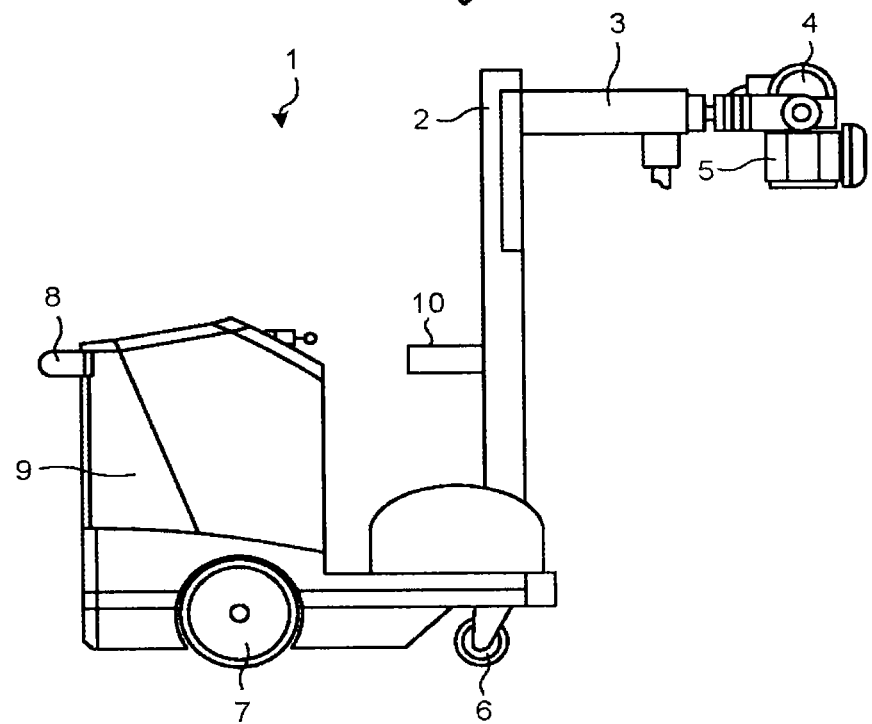

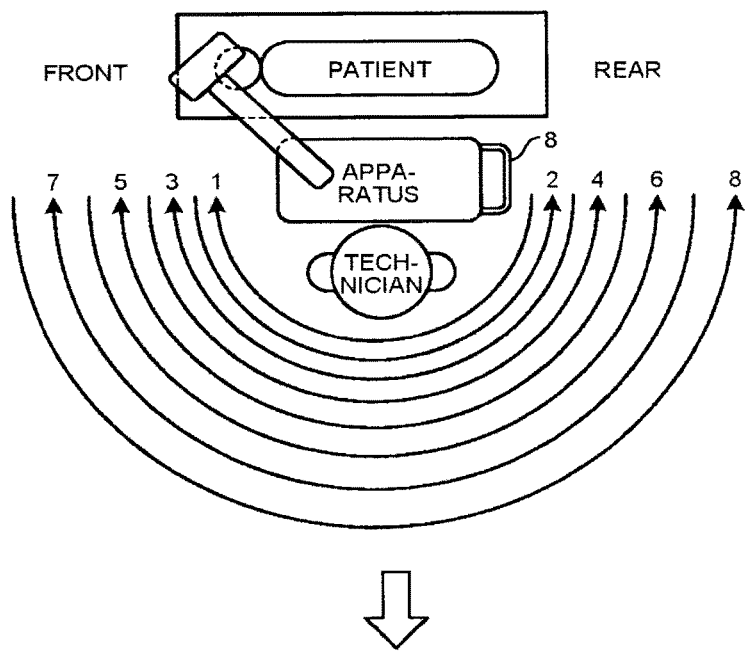

(B)

| 1 | MOVE TO FRONT<br>SETTING OF X-RAY IRRADIATION POSITION<br>(POSITIONING OF X-RAY TUBE/IRRADIATION FIELD APERTURE) |
| --- | --- |
| 2 | MOVE TO REAR<br>FPD (TAKING OUT/REAR) |
| 3 | MOVE TO FRONT<br>FPD (SETTING) |
| 4 | MOVE TO REAR<br>X-RAY IMAGING |
| 5 | MOVE TO FRONT<br>FPD (COLLECTING) |
| 6 | MOVE TO REAR<br>FPD (STORING/REAR) |
| 7 | MOVE TO FRONT<br>HOUSING X-RAY TUBE<br>TURN OFF IMAGING CONTROL SYSTEM |
| 8 | MOVE TO REAR<br>TAKING AWAY APPARATUS |

MOBILE X-RAY DIAGNOSTIC APPARATUS

CROSS-REFERENCE TO RELATED APPLICATIONS

This application is based upon and claims the benefit of priority of the prior Japanese Patent Application No. 2014-139909, filed on Jul. 7, 2014, the entire contents of which are incorporated herein by reference. The entire contents of the prior Japanese Patent Application No. 2015-102160, filed on May 19, 2015, are also incorporated herein by reference.

FIELD

Embodiments described herein relate generally to a mobile X-ray diagnostic apparatus.

BACKGROUND

Conventionally, mobile X-ray-diagnostic apparatuses that are moved to a sickroom to take X-ray images have been known. For example, a mobile X-ray-diagnostic apparatus includes an X-ray tube that generates X-rays, an X-ray movable collimator that adjusts a radiation field of X-rays generated by the X-ray tube, a support mechanism that supports the X-tube and the X-ray movable collimator, and an apparatus main body that performs various kinds of controls of the mobile X-ray-diagnostic apparatus, and wheels to move the apparatus. The mobile X-ray-diagnostic apparatus is moved to a sickroom by an operator, and performs X-ray imaging of a subject that is laid on a bed and that cannot move easily (for example, during intravenous infusion, being bedridden, having walking difficulty due to injury of both legs, and the like). After X-ray imaging is finished, the mobile X-ray-diagnostic apparatus is moved outside the sickroom.

BRIEF DESCRIPTION OF THE DRAWINGS

FIG. 1 depicts one example of an entire configuration of a mobile X-ray-diagnostic apparatus according to a first embodiment;

FIG. 2 depicts one example of a flow of imaging an X-ray image using a mobile X-ray-diagnostic apparatus according to a conventional technique;

DETAILED DESCRIPTION

First Embodiment

Figure 3A:
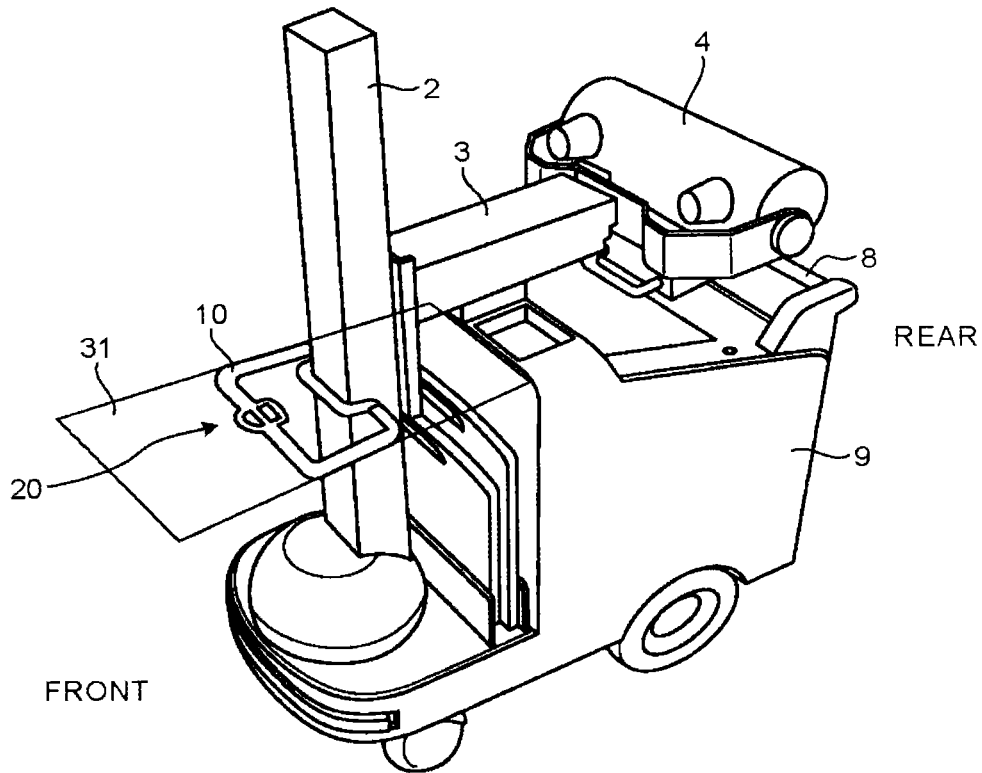
FIG. 3A is a diagram for explaining problems of operating switches on a front side.

First, one example of an entire configuration of a mobile X-ray-diagnostic apparatus according to a first embodiment is explained using FIG. 1. FIG. 1 depicts one example of an entire configuration of a mobile X-ray-diagnostic apparatus 1 according to the first embodiment. IN FIG. 1, FIG. 1(A) depicts a state in which an X-ray tube is housed, and FIG. 1(B) depicts a state at the time of acquiring an X-ray image. As depicted in FIG. 1(A), the mobile X-ray-diagnostic apparatus 1 includes a support column 2, an arm 3, an X-ray tube 4, an X-ray movable collimator 5, front wheels 6, rear wheels 7, a first operating handle 8, an apparatus main body 9, and a second operating handle 10.

The support column 2 is rotatably held about an axis in a vertical direction, and supports the arm 3 at the other end thereof. For example, as depicted in FIG. 1(A), the support column 2 is arranged on a front side (on a front wheel 6 side) of the mobile X-ray-diagnostic apparatus 1, and supports the arm 3 by connecting one end of the arm 3. The support column 2 is arranged on the mobile X-ray-diagnostic apparatus 1 in such a manner that a longitudinal direction is parallel to the vertical direction. For example, on the support column 2, a rail is arranged along the longitudinal direction, and one end of the arm 3 is connected to the arranged rail. The arm 3 holds an X-ray generator at one end. Specifically, the arm is connected to the support column 2 at one end, and has the X-ray tube 4 and the X-ray movable collimator 5 arranged at the other end. The arm 3 is connected to the support column 2 so as to be slidable in a vertical direction. For example, a rail is arranged on the support column 2, and one end of the arm 3 is connected to the rail and moves on the rail, thereby sliding in the vertical direction. Moreover, the arm 3 is expandable in a direction perpendicular to the longitudinal direction of the support column 2. Specifically, at the time of housing the X-ray tube 4, the arm 3 contracts and houses the X-ray tube 4 so as not to stick out, and at the time of taking an X-ray image, the arm 3 expands so as to allow the X-ray tube 4 to reach as far as possible. The arm 3 is also called a holding unit.

The X-ray tube 4 is connected to a high voltage generator (not shown) that is included in the apparatus main body 9, and uses high voltage supplied by the high voltage generator to generate X-rays. The X-ray tube 4 is also called an X-ray generator. Furthermore, as the X-ray generator, in addition to the X-ray tube 4, at least one of the high voltage generator and the X-ray movable collimator 5 is included in some cases. The X-ray movable collimator includes, for example, two pairs of movable limiting blades, and adjusts a radiation field of X-rays by opening and closing the movable limiting blades of each pair. That is, in the X-ray movable collimator 5, the movable limiting blades are opened and closed so that an X-ray that is emitted in a conical form by the X-ray tube 4 is irradiated in a predetermined radiation field. In the X-ray movable collimator 5, an illumination lamp that illuminates a radiation field of X-rays that is adjusted by the movable limiting blades may be provided. That is, by turning two knobs to adjust the movable limiting blades in a state in which the illumination lamp is lit, an operator can adjusts the aperture degree of the movable limiting blades while viewing the radiation field.

The front wheels 6 are wheels that turn freely, and are, for example, a pair of casters and the like. The rear wheels 7 are driving wheels to which a motor not shown or the like is connected, and drive according to operation by an operator. For example, the motor is driven when a pressure sensor provided at the first operating handle 8 detects predetermined pressure, or when an operating switch provided near the first operating handle 8 is pressed, and the rear wheels 7 is driven by a moving force by the motor. Moreover, driving of the rear wheels 7 is controlled by an operating switch provided near the second operating handle 10 also. Details of the operating switch provided near the second operating handle 10 and control of driving of the rear wheels 7 are described later.

Furthermore, although a case in which only the rear wheels 7 are the driving wheels in the mobile X-ray-diagnostic apparatus 1 shown in FIG. 1 is explained as an example, the embodiment is not limited thereto, and for example, the front wheels 6 may also be the driving wheels. Alternatively, the front wheels 6 may be the driving wheels and the rear wheels 7 may be the wheels that can turn freely. That is, the front wheels 6 and the rear wheels 7 may be driven by the respective operating switches provided near the first operating handle 8 and the second operating handle 10, or only the front wheels 6 may be driven thereby. Moreover, positions of wheels of the mobile X-ray-diagnostic apparatus 1 may be at arbitrary positions, and wheels may not be distinguished as the front wheels 6 and the rear wheels 7. In such a case, wheels that enable to move the mobile X-ray-diagnostic apparatus 1 are driven by the respective operating switches arranged near the first operating handle 8 and the second operating handle 10.

The first operating handle 8 is a handle that is operated when an operator moves the mobile X-ray-diagnostic apparatus 1. For example, the operator can move the mobile X-ray-diagnostic apparatus 1 forward and backward by pressing the operating switch in a state in which the first operating handle 8 is griped. Alternatively, the first operating handle 8 can include a pressure sensor, and detect a direction toward which the operator operates (for example, forward movement when the operator stands on a rear side (rear wheels 7 side) of the apparatus main body 9, grips the first operating handle 8, and pushes the first operating handle 8; backward movement when the operator pulls the first operating handle 8; and the like) to drive a motor in a desirable direction. The mobile X-ray-diagnostic apparatus 1 is controlled such that brakes are applied when the operating switch described above is stopped being pressed, or when detection of pressure by the pressure sensor stops.

The second operating handle 10 is a handle that is operated when an operator moves the mobile X-ray-diagnostic apparatus 1. For example, the operator can move the mobile X-ray-diagnostic apparatus 1 forward and backward by pressing the operating switch in a state in which the second operating handle 10 is griped. Movement the mobile X-ray-diagnostic apparatus 1 using the second operating handle 10 is described later.

The apparatus main body 9 includes a controller that controls respective components of the mobile X-ray-diagnostic apparatus 1, a storage that stores various kinds of data, a battery that accumulates power supplied from an external unit, an input circuitry that accepts various kinds of operations, a display that displays various kinds of information, and the like. The apparatus main body 9 controls various kinds of processing related to movement of the mobile X-ray-diagnostic apparatus 1, and various kinds of processing related to imaging of an X-ray image. For example, the apparatus main body 9 controls the high voltage generator according to an instruction of an operator that has been transferred from the input circuitry arranged on an upper surface of the apparatus main body 9, and adjusts a voltage to be supplied to the X-ray tube 4, thereby controlling a dose or ON/OFF of X-rays to be irradiated to a subject. Moreover, for example, the apparatus main body 9 controls the X-ray movable collimator 5 according to an instruction of the operator, and adjusts the aperture degree of the movable limiting blades included in the X-ray movable collimator 5, thereby controlling a radiation field of X-rays to be irradiated to a subject. Furthermore, the apparatus main body 9 drives the motor equipped therein according to a pressure detected by the pressure sensor provided at the first operating handle 8, or an operation accepted by the operating switch, to drive the rear wheels 7 by the moving force of the motor. The apparatus main body 9, the front wheels 6, and the rear wheels 7 are also referred to as a main body collectively.

In the above example, a case in which the rear wheels 7 are driven according to an operation that is accepted by the respective operating switches provided at the first operating handle 8 and the second operating handle 10 has been explained as an example. However, the embodiment is not limited thereto, and the front wheels 6 may be driven according to an operation that is accepted by the respective operating switches provided at the first operating handle 8 and the second operating handle 10. In such a case, the apparatus main body 9 includes a motor to drive the front wheels 6, and drives the motor according to an operation that is accepted by the respective operating switches provided at the first operating handle 8 and the second operating handle 10, to drive the front wheels 6. Alternatively, the apparatus main body 9 drives wheels to move the mobile X-ray-diagnostic apparatus 1, by driving the motor according to an operation that is accepted by the respective operating switches provided at the first operating handle 8 and the second operating handle 10.

Moreover, the apparatus main body 9 controls an image-data generation processing, an image processing, an analysis processing, and the like according to an instruction of an operator. Furthermore, the apparatus main body 9 controls to display a graphical user interface (GUI) to accept an instruction of an operator, an image stored in the storage, and the like on a display of the display. In the following, a flow of imaging an X-ray image using the mobile X-ray-diagnostic apparatus 1 is explained. For example, the mobile X-ray-diagnostic apparatus 1 is placed in a corridor on each floor and the like of a hospital during standby, and is charged according to a battery capacity. When using, the mobile X-ray-diagnostic apparatus 1 is unlocked with a dedicated key or the like, and is moved to a sickroom and the like by operating the first operating handle 8 by an operator, and by driving the rear wheels 7 by a driving button (or a pressure sensor and the like).

When moved to a sickroom, the operator turns the support column 2 about the longitudinal direction as indicated in FIG. 1(B), to direct the X-ray tube 4 and the X-ray movable collimator 5 toward the front of the apparatus main body 9. The operator then expands the arm 3 to position the X-ray tube 4 at a position at which an X-ray is irradiated on an imaged part of a subject. The operator makes adjustment so that the image part is positioned in the radiation field, by using a switch or a knob provided in the X-ray movable collimator 5. Thereafter, an image recording medium such as a flat panel detector (FPD) and a cassette, is set between the imaged part of the subject and a bed, and an X-ray image is taken.

As described, the mobile X-ray-diagnostic apparatus 1 is moved to a sickroom in which a subject is present when it is used, and an FPD, a cassette, or the like is set between an imaged part of the subject and a bed, positions of the X-ray tube 4 and a radiation field with respect to the imaged part are adjusted, and an X-ray image is taken. At the imaging, there is a case in which the operator moves back and forth between the front side and the rear side of the apparatus, and a problem of taking labor has conventionally been concerned. FIG. 2 depicts on example of a flow of imaging an X-ray image using the mobile X-ray-diagnostic apparatus according to a conventional technique. FIG. 2(A) depicts movement of an operator between the front side and the rear side relative to the apparatus. Moreover, FIG. 2(B) depicts processing corresponding to each number in FIG. 2(A). The front side in FIG. 2 signifies a side on which a supporting mechanism such as an arm and a support column to support the X-ray tube is provided, and the rear side signifies a side on which an operating handle (corresponding to the first operating handle 8) to mote the apparatus.

For example, an operator moves back and forth between the front side and the rear side for eight times as shown in FIG. 2(A) when taking an X-ray image by the mobile X-ray-diagnostic apparatus. That is, as shown in FIG. 2(B), the operator moves the apparatus to a sickroom, while operating the operating handle (the first operating handle 8) on the rear side. When moved to a sickroom, the operator moves to the front side to set an X-ray irradiation position (for example, positioning of the X-ray tube/a radiation field) ("1" in FIG. 2).

When setting of the X-ray irradiation position is finished, the operator moves to the rear side, and takes out an FPD that is stored on the rear side ("2" in FIG. 2), and moves to the front side to set the FED ("3" in FIG. 2). Thereafter, the operator moves to the rear side and takes an X-ray image ("4" in FIG. 2), and moves to the front side to collect the FPD after imaging ("5" in FIG. 2).

When the FPD is collected, the operator moves to the rear side and stores the collected FPD in a storage space ("6" in FIG. 2). Thereafter, the operator moves to the front side and houses the X-ray tube and turns off the power of an imaging control system ("7" in FIG. 2), and then moves to the rear side and goes out of the sickroom holding the operating handle ("8" in FIG. 2). As described, in the conventional mobile X-ray-diagnostic apparatus, an operator moves back and forth between the front side and the rear side when taking an X-ray image, and it takes labor.

Therefore, to tackle this problem, a mobile X-ray-diagnostic apparatus in which an operating handle (corresponding to the second operating handle in this application) on the front side is arranged on a support column to be used so that movement between the front side and the rear side is reduced can be considered. This enables an operator to move the apparatus out of a sickroom without moving to the rear side at "8" in the imaging flow.

Figure 3B:
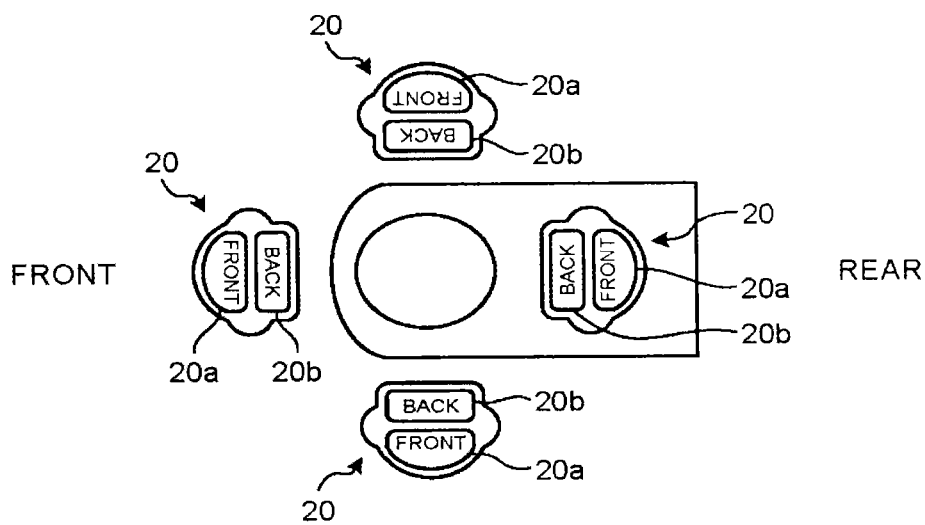
FIG. 3B is a diagram for explaining problems of the operating switches on the front side.

However, when an operating switch is arranged near the operating handle on the front side described above, the operability can be degraded depending on how it is arranged. Specifically, if operating switches to move the mobile X-ray-diagnostic apparatus forward and backward are arranged at positions shifted in a horizontal direction (direction perpendicular to a direction of a rotation axis of the support column), visual positional relation changes according to turns of the support column. This makes the operational feeling less intuitive, and the operability can be degraded. In the following, problems of the operating switches on the front side are explained using FIG. 3A and FIG. 3B. FIG. 3A and FIG. 3B are diagrams for explaining problems of the operating switches on the front side.

For example, an operating handle (the second operating handle 10) on the front side is arranged on the support column 2 as shown in FIG. 3A, and has a holding portion that is held by an operator similarly to an operating handle (the first operating handle 8) on the rear side. If operating switches included in input equipment 20 on the front side are arranged at positions shifted on a horizontal plane 31, visual positional relation of the operating switches changes when the support column 2 turns, and this makes the operational feeling less intuitive. For example, as shown in FIG. 3A, when the input equipment 20 includes two operating switches for moving forward and moving backward, and if those are arranged such that the distances from a floor are the same, and that one is shifted toward the front side and the other is shifted toward the rear side, visual positional relation changes when the support column 2 turns.

In the following, one example is explained using FIG. 3B. FIG. 3B depicts the input equipment 20 viewed from above when the support column 2 of the mobile X-ray-diagnostic apparatus shown in FIG. 3A turns. Moreover, in the input equipment 20 shown in FIG. 3B, an operating switch 20*a* indicated as "FRONT" is an operating switch for moving forward (moving toward the front side), and an operating switch 20*b* indicated as "BACK" is an operating switch for moving backward (moving to the rear side). That is, an operator presses the operating switch 20*a* while operating the operating handle on the front side, when wishing to drive the mobile X-ray-diagnostic apparatus toward the front side. On the other hand, the operator presses the operating switch 20*b* while operating the operating handle on the front side, when wishing to drive the mobile X-ray-diagnostic apparatus toward the rear side.

When the arm 3 is in a stored state (the state shown in FIG. 3A), as shown in the input equipment 20 on a left side of FIG. 3B, the operating switch 20*a* is positioned on the front side and the operating switch 20*b* is positioned on the rear side. For example, when an operator operates standing on the front side, a closer side corresponds to the operating switch 20*a* and a farther side corresponds to the operating switch 20*b*. On the other hand, when the support column 2 turns by 180 degrees, as shown in the input equipment 20 on a right side of FIG. 3B, the operating switch 20*a* is positioned on the rear side, and the operating switch 20*b* is positioned on the front side. That is, when the operator operates standing on the front side, the closer side corresponds to the operating switch 20*b*, and the farther side corresponds to the operating switch 20*a*. Moreover, as shown in the input equipment. 20 on an upper side and the input equipment 20 on a lower side of FIG. 3B, the visual positional relation of the operating switch 20a and the operating switch 20b changes according to a turned state of the support column 2. Such a change of the visual positional relation of the operating switches according to a turn of the support column 2 occurs not only when the operating switches are shifted to the front side and to the rear side, but also when the operating switches are shifted to a right side and a left side of the apparatus.

Figure 4A:
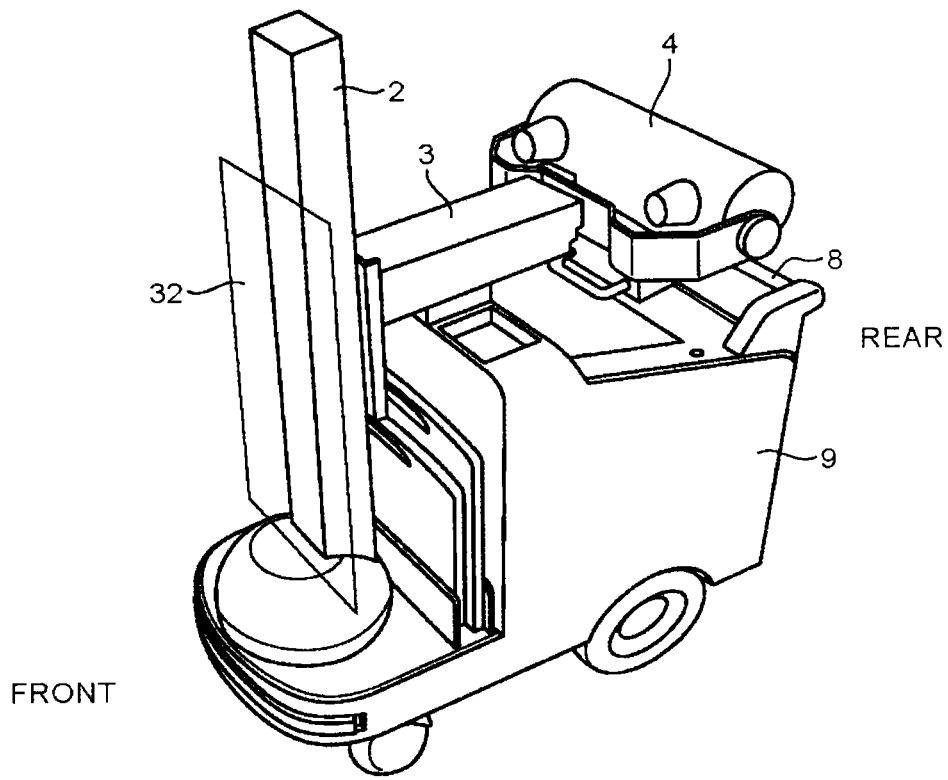
FIG. 4A is a diagram for explaining an overview of an input equipment according to the first embodiment.
Figure 4B:
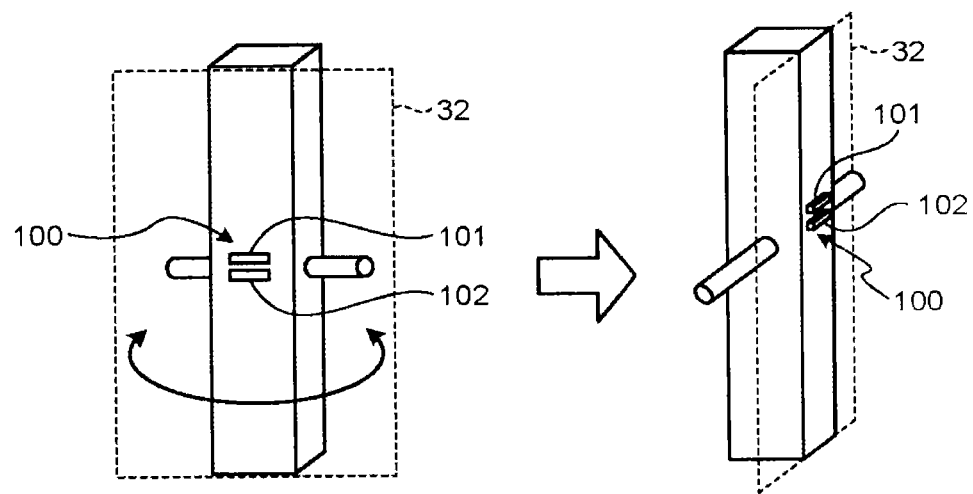
FIG. 4B is a diagram for explaining an overview of the input equipment according to the first embodiment.

As described above, at a use of the mobile X-ray-diagnostic apparatus, the operability in movement can be degraded. Therefore, the mobile X-ray-diagnostic apparatus 1 according to the present application enables to improve the operability in movement, by providing input equipment that includes operating switches enabling to drive the apparatus easily from any position irrespective of a turned state of the support column 2. In the following, an overview of an input equipment according to the first embodiment is explained using FIG. 4A and FIG. 4B. FIG. 4A and FIG. 4B are diagrams for explaining the overview of the input equipment according to the first embodiment.

Specifically, the mobile X-ray-diagnostic apparatus 1 according to the first embodiment includes input equipment in which operating switches are arranged at positions shifted in a vertical direction (direction parallel to the direction of the rotation axis of the support column). For example, the mobile X-ray-diagnostic apparatus 1 according to the first embodiment has the operating switches that are arranged at positions shifted in the vertical direction on a vertical plane 32 shown in FIG. 4A. As one example, as shown in FIG. 4B, the mobile X-ray-diagnostic apparatus 1 includes an input equipment 100 in which an operating switch 101 is arranged on an upper side and an operating switch 102 is arranged on a lower side compared to the operating switch 101 on the vertical plane 32.

As described, by arranging the multiple operating switches at positions shifted in the vertical direction (perpendicular direction), even if the support column 2 turns, visual positional relation of the operating switches does not change, and the operational feeling is intuitive, and the operability in movement can be improved. For example, as shown in a drawing on a left side of FIG. 4B, the mobile X-ray-diagnostic apparatus 1 includes the operating switch 101 on the upper side and the operating switch 102 on the lower side in the direction parallel to the direction of rotation axis of the support column 2. Thus, even when the support column 2 is in any turned stated, the operating switch 101 is on the upper side and the operating switch 102 is on the lower side. As one example, as shown in a drawing on a right side of FIG. 4B, even if the support column 2 turns by 90°, the operating switch 101 is on the upper side and the operating switch 102 is on the lower side. In addition, as for the operating switches that are arranged vertically, by arranging an operating switch to move the mobile X-ray-diagnostic apparatus 1 forward on the upper side, and an operating switch to move the mobile X-ray-diagnostic apparatus 1 backward on the lower side, the relation of superiority and inferiority in meaning corresponds thereto, and the operational feeling becomes more intuitive. That is, when the superiority and inferiority in meaning of "forward and backward" and "upper and lower" are considered, "forward" and "upper" have a "superior (positive)" image, and "backward" and "lower" have a "inferior (negative)" image. Therefore, by arranging the switches associating with these, an operator can have more intuitive operational feeling.

As described above, the operating switch 101 and the operating switch 102 are arranged at positions shifted in the vertical direction, thereby improving the operability in movement. Such a structure is explained more specifically. The operating switch 101 and the operating switch 102 are arranged along the rotation axis of the support column 2. The operating switch 101 and the operating switch 102 are arranged such that distances from a floor are fixed irrespective of a turned state of the support column 2.

Figure 5:
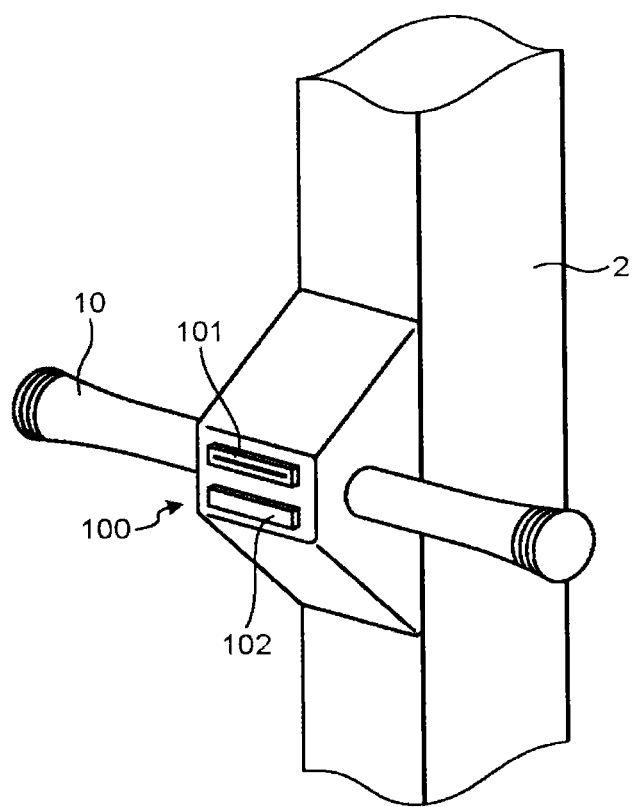
FIG. 5 depicts one example of a second operating handle and the input equipment according to the first embodiment.

The second operating handle and the input equipment 100 according to the first embodiment are arranged such that an operator can operate the operating switch 101 and the operating switch 102 while doing the operation related to driving, holding the second operating handle 10. FIG. 5 depicts one example of the second operating handle 10 and the input equipment 100 according to the first embodiment. In FIG. 5, a case in which on side surfaces of the support column 2, the input equipment 100 and the like are arranged on a side surface opposing to a side surface at which the arm 3 is supported is depicted.

For example, a joining unit that includes the input equipment having the operating switch 101 and the operating switch 102 is joined onto a side surface of the support column 2. The operating switch 101 and the operating switch 102 are arranged on a plane parallel to the side surface of the support column 2 on which the joining unit is joined, and the second operating handle 10 is arranged on each of two sides of the joining unit. That is, the operating switch 101 and the operating switch 102 are arranged on a side surface of a column that is substantially perpendicular to a floor. The operating switch 101 and the operating switch 102 are arranged at positions shifted in the vertical direction as shown in FIG. 5. For example, as the operating switch 101 (the operating switch on the upper side in the vertical direction), an operating switch for forward movement to drive the mobile X-ray-diagnostic apparatus 1 toward the front side is arranged, and as the operating switch 102 (the operating switch on the lower side in the vertical direction), an operating switch for backward movement to drive the mobile X-ray-diagnostic apparatus 1 toward the rear side is arranged.

Figure 6:
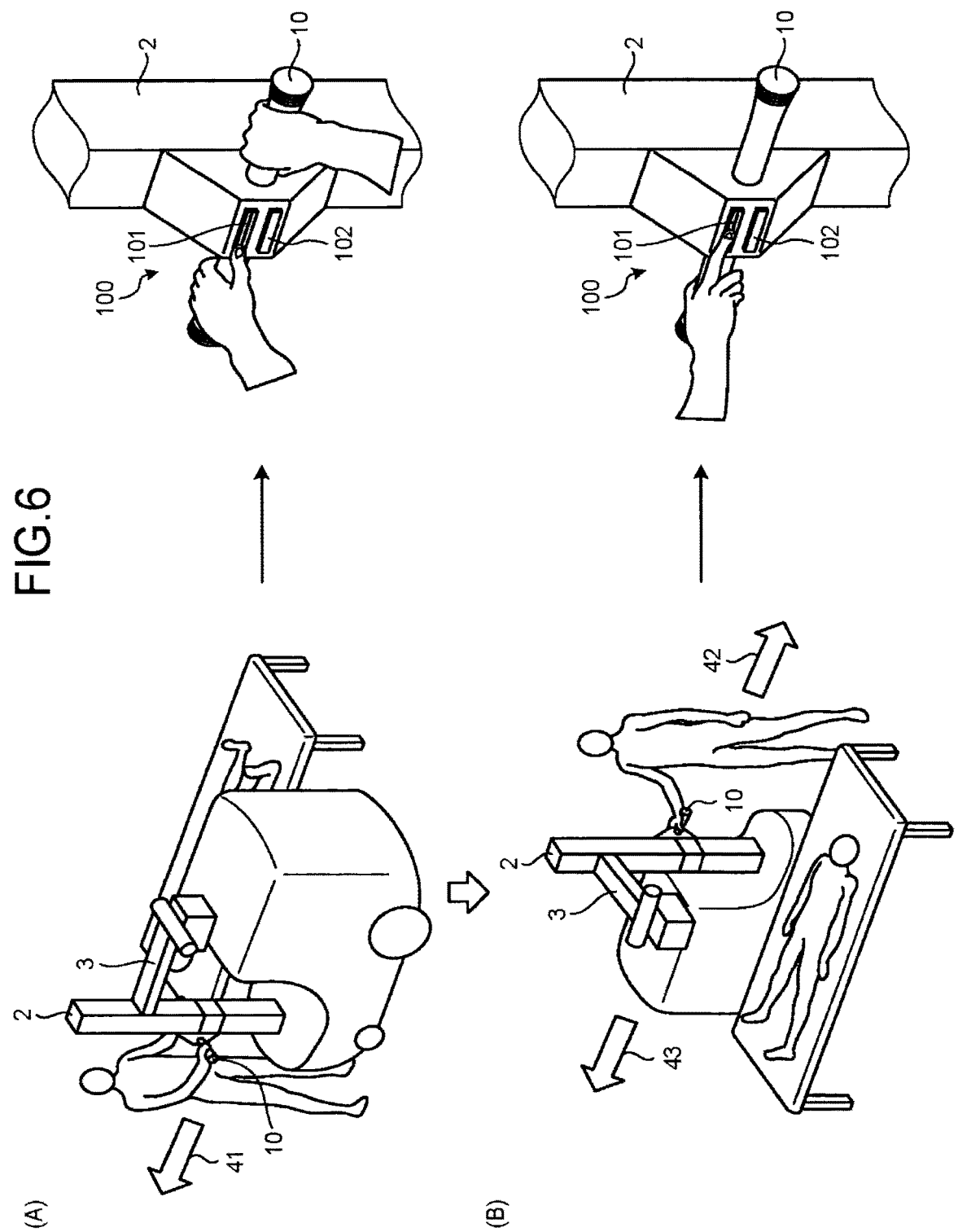
FIG. 6 is a diagram for explaining a use example of the mobile X-ray-diagnostic apparatus according to the first embodiment.

By arranging the operating switches as described above, the operational feeling becomes intuitive irrespective of a turned state of the support column 2, and operation of the operating switches can be easily performed while holding the operating handle. FIG. 6 is a diagram for explaining a use example of the mobile X-ray-diagnostic apparatus 1 according to the first embodiment. Mobile X-ray-diagnostic apparatuses are often used in a narrow sickroom, and there are many cases in which the way of operating the apparatus in a sickroom is limited. For example, there is a case in which the mobile X-ray-diagnostic apparatus must be operated in a small space beside a bed on which a subject is laid. In such a case, the operator is required to move the mobile X-ray-diagnostic apparatus safely, paying attention to the surroundings, to take an X-ray image.

Even in such a case, for example, in the mobile X-ray-diagnostic apparatus 1 according to the first embodiment, as shown in FIG. 6(A), paying attention to the surroundings, an operator can move the apparatus into a narrow space beside a bed by pressing the operating switch 101 while holding the second operating handle 10 to drive the apparatus in a direction (toward the front side) of an arrow 41. In the mobile X-ray-diagnostic apparatus 1 is configured such that an operator can press the operating switch 101 while holding the second operating handle 10 firmly as shown in a drawing on a right side of FIG. 6(A).

Furthermore, as shown in FIG. 6(B), the operator can drive the apparatus to an imaged part, moving the apparatus in a direction of an arrow 42 or an arrow 43, with the support column 2 turned such that the arm 3 is positioned on a subject side, by pressing the operating switch 101 and the operating switch 102 while being on the front side of the apparatus and watching a state of a subject. In the mobile X-ray-diagnostic apparatus 1, as shown in a drawing on a right side of FIG. 6(B), because the positional relation of the operating switch 101 and the operating switch 102 is always invariable irrespective of a turned state of the support column 2, the operator can operate the operating switch 101 and the operating switch 102 without looking at a hand to check driving directions of the operating switches. This enables the operator to operate the mobile X-ray-diagnostic apparatus 1 while focusing on the subject all the time.

As above, one example of the input equipment 100 that includes the operating switch 101 and the operating switch 102 has been explained. However, the operating switches included in the input equipment 100 are not limited to the example described above (for example the operating switches depicted in FIG. 5). That is, the input equipment 100 provided in the mobile X-ray-diagnostic apparatus 1 can take various forms as long as operating switches are arranged at positions shifted in the vertical direction. In the following, modifications of the input equipment 100 are explained using FIG. 7A to FIG. 7F. FIG. 7A to FIG. 7F depict modifications of the input equipment 100 according to the first embodiment.

For example, the input equipment 100 may include the operating switch 101 and the operating switch 102 that are formed long from side to side. That is, the input equipment 100 shown in FIG. 7A enables easy operation of the operating switch 101 and the operating switch 102 while holding the second operating handle 10 even when the joining unit that is joined to the support column 2 is enlarged to widen a space in the second operating handle 10 to facilitate the operation thereof with both hands.

Figure 7A:
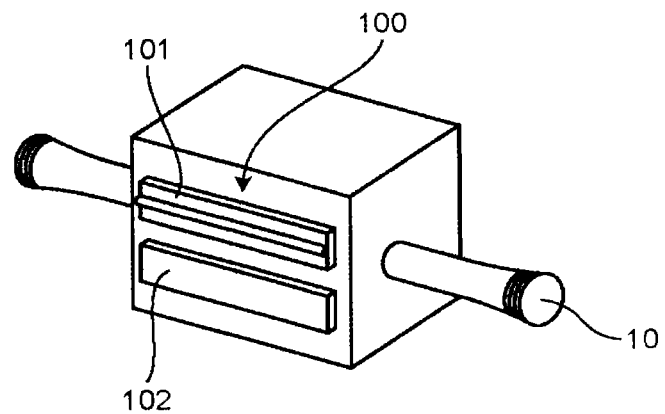
FIG. 7A depicts a modification of the input equipment according to the first embodiment.
Figure 7B:
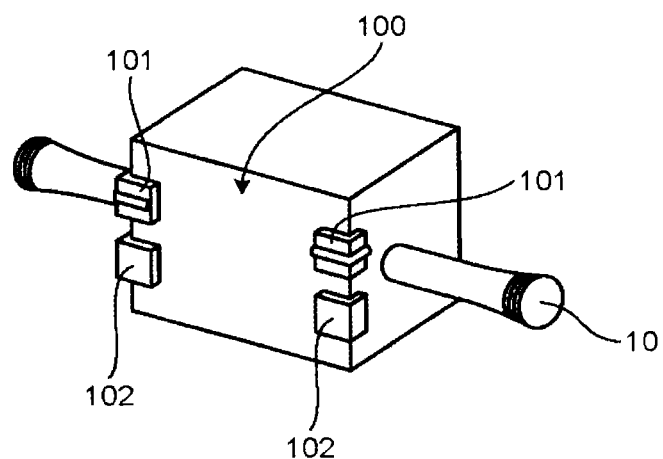
FIG. 7B depicts a modification of the input equipment according to the first embodiment.

Moreover, the input equipment 100 may have the operating switches divided into multiple parts. For example, as shown in FIG. 7B, the operating switch 101 and the operating switch 102 are divided into two parts, and divided operating switches are arranged near the second operating handle 10 that is arranged on both sides of the joining unit joined to the support column 2.

Figure 7C:
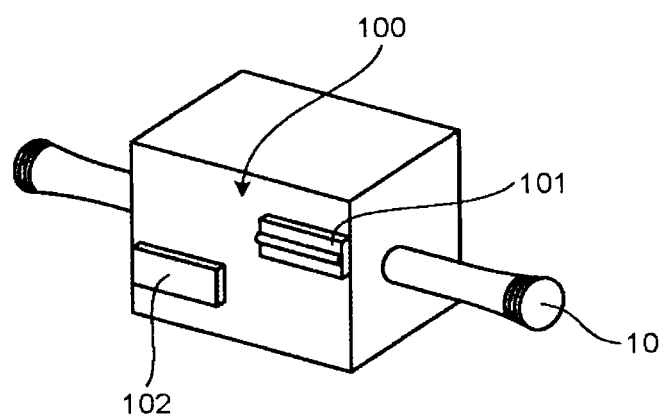
FIG. 7C depicts a modification of the input equipment according to the first embodiment.

Furthermore, in the input equipment 100, for example, as shown in FIG. 7C, the operating switch 101 and the operating switch 102 may be formed at positions shifted in the vertical direction, and in the horizontal direction also. Even when formed in such a manner, the positional relation in the vertical direction of the operating switch 101 and the operating switch 102 is invariable irrespective of a turned state of the support column 2, and therefore, the operational feeling can be intuitive.

Figure 7D:
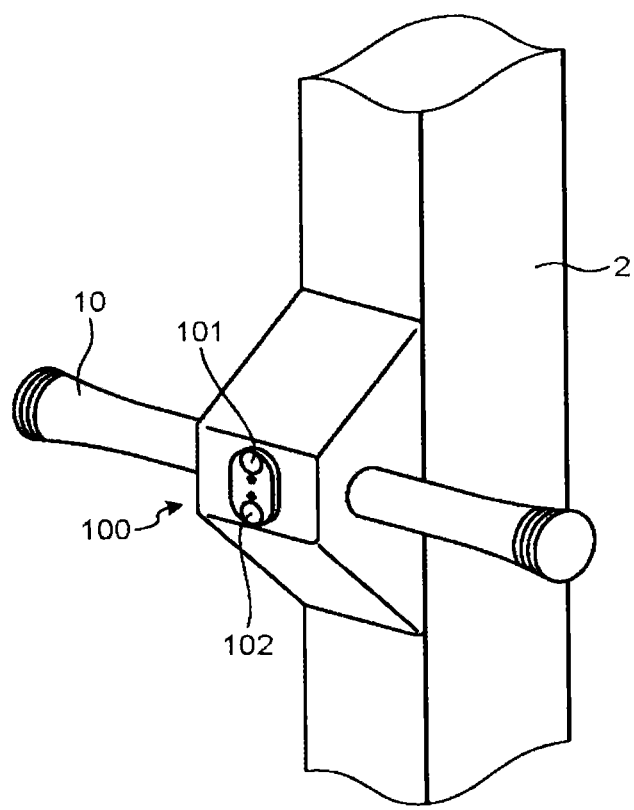
FIG. 7D depicts a modification of the input equipment according to the first embodiment.

Moreover, the input equipment 100 is not limited to have simple press-down buttons, and various kinds of switches can be included. For example, as shown in FIG. 7D, the input equipment 100 may include a seesaw switch in which the operating switch 101 for forward movement is arranged on an upper side, and the operating switch 102 for backward movement is arranged on a lower side.

Figure 7E:
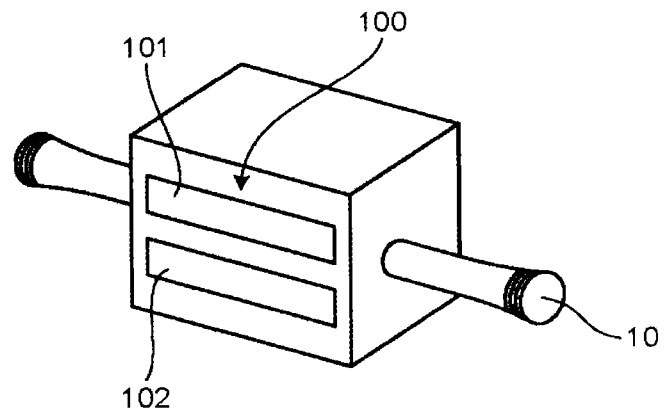
FIG. 7E depicts a modification of the input equipment according to the first embodiment.

Furthermore, the input equipment 100 is not limited to buttons and switches, and may include a touch panel. For example, as shown in FIG. 7E, the input equipment 100 includes two touch panels that are arranged at positions shifted in the vertical direction, and a touch panel on an upper side accepts an operation for forward movement similarly to the operating switch 101, and a touch panel on the lower side accepts an operation for backward movement similarly to the operating switch 102. That is, while holding the second operating handle 10, the operator can drive the apparatus toward the front side by touching the touch panel on the upper side, and drives the apparatus to the rear side by touching the touch panel on the lower side.

Figure 7F:
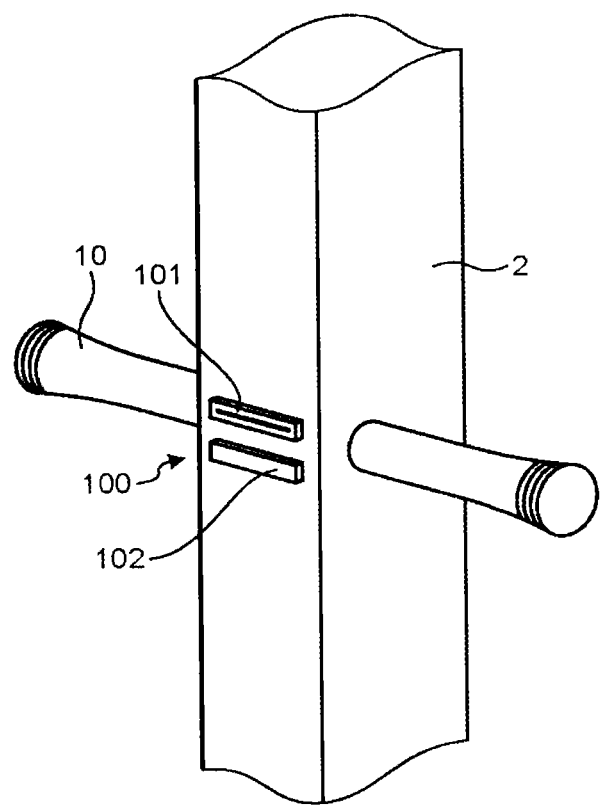
FIG. 7F depicts a modification of the input equipment according to the first embodiment.

In each example described above, a case in which the joining unit that has the input equipment 100 is joined to the support column 2 has been explained. However, the embodiment is not limited thereto, and the input equipment 100 may be arranged on the support column 2. Specifically, the input equipment 100 is arranged on a side surface of the support column 2 that is substantially perpendicular to a floor. That is, the input equipment 100 is arranged on at least one side surface that has a plane in the horizontal direction in the support column 2. For example, as shown in FIG. 7F, the operating switch 101 and the operating switch 102 are arranged at positions shifted in the vertical direction on a side surface opposing to a side surface at which the arm 3 is supported on the support column 2. Furthermore, the second operating handle 10 is arranged on side surfaces on both sides that are perpendicular to the side surface on which the respective operating switches are arranged. Thus, the front side can be formed compact.

As described above, according to the first embodiment, the X-ray generator (for example, the X-ray tube 4, and the like) generates X-rays. The arm 3 holds the X-ray generator at one end. The apparatus main body 9 has wheels (for example, the front wheels 6 and the rear wheels 7). The support column 2 is supported turnably about the axis in the vertical direction, and supports the other end of the arm 3. At least two operating switches 101 and 102 are arranged at positions shifted in the vertical direction to the support column 2, and controls driving of the apparatus main body 9. Therefore, in the mobile X-ray-diagnostic apparatus 1 according to the first embodiment, the positional relation of multiple operating switches does not change even when the support column 2 turns, and it is possible to let an operator grasp the operating direction intuitively, and to improve the operability related to movement.

As described, by arranging the operating switch 101 and the operating switch 102 according to the first embodiment always along the rotation axis direction (vertical direction) of the support column 2, an operator can grasp the operational feeling of the operating switches intuitively in any state. As a conventional technique in which switches are arranged in a vertical direction as described, a technique in which slight movement switches are arranged on an X-ray movable collimator has been available. However, because the X-ray movable collimator rotates arbitrarily about a longitudinal direction of an arm as the rotation axis, the operating switches are not always aligned in the vertical direction. Therefore, with the above slight movement switches, the operational feeling can be not intuitive.

Moreover, according to the first embodiment, at least two operating switches constituting the input equipment 100 are arranged such that distance from a floor are invariable irrespective of a turned state of the support column 2. Therefore, the mobile X-ray-diagnostic apparatus 1 according to the first embodiment enables to make the positional relation of the operating switches invariable.

Second Embodiment

In the first embodiment described above, a case in which the input equipment 100 includes multiple operating switches (the operating switch 101 for forward movement and the operating switch 102 for backward movement) or touch panels has been explained. In a second embodiment, a case in which driving of the apparatus is controlled with a single touch panel is explained.

Figure 8A:
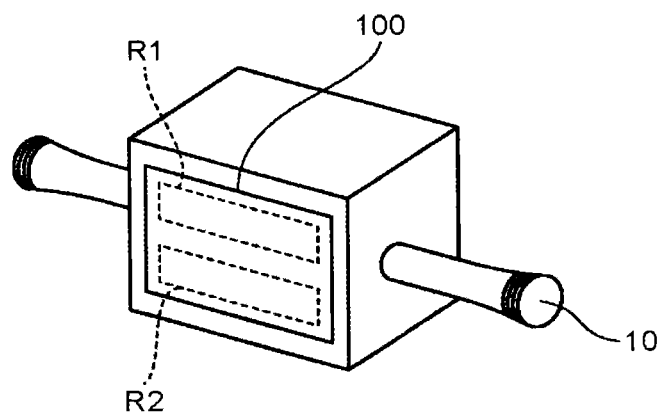
FIG. 8A depicts one example of an input equipment according to a second embodiment.
Figure 8B:
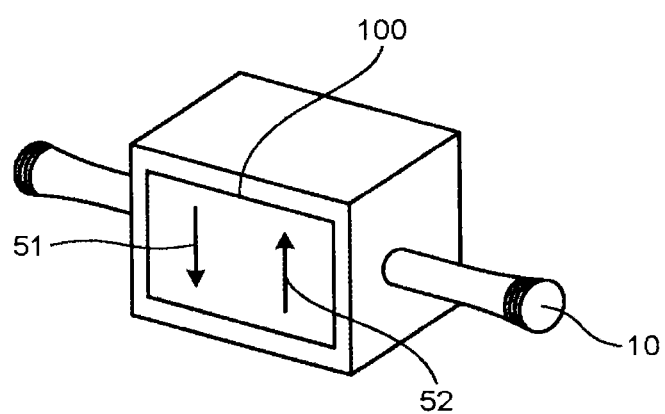
FIG. 8B depicts one example of an input equipment according to a second embodiment.

Specifically, the input equipment 100 in the second embodiment is arranged on the support column 2, and accepts an operation for upward and an operation for downward in the vertical direction, thereby controlling driving of the apparatus main body 9 in different directions. FIG. 8A and FIG. 8B depict one example of the input equipment 100 according to the second embodiment. For example, as depicted in FIGS. 8A and 8B, the input equipment 100 according to the second embodiment is a single unit of touch panel that is mounted on the joining unit joined to the support column 2. The touch panel functioning as the input equipment 100 controls the apparatus main body 9 to move forward and backward by accepting a predetermined operation from an operator.

For example, as depicted in FIG. 8A, the input equipment 100 includes a region R1 on the upper side and a region R2 on the lower side in the vertical direction in the touch panel, and controls driving of the apparatus by accepting an operation to each of the regions. For example, the input equipment 100 controls forward movement of the apparatus by accepting a touch operation to the region R1, and controls backward movement of the apparatus by accepting a touch operation to the region R2. That is, the operator drives the apparatus toward the front side by touching the region R1, and drives the apparatus toward the rear side by touching the region R2 on the touch panel of the input equipment 100.

Furthermore, as depicted in FIG. 8B, the input equipment 100 controls a driving direction according to a direction of a swipe operation on the touch panel. For example, the input equipment 100 controls forward movement of the apparatus by accepting a swipe operation to the upper side (for example, a direction of an arrow 52 in FIG. 8B) in the vertical direction, and controls backward movement of the apparatus by accepting a swipe operation to the lower side (for example, a direction of an arrow 51 in FIG. 8B) in the vertical direction. That is, the operator drives the apparatus toward the front side by swiping in the direction of the arrow 52, and drives the apparatus toward the rear side by swiping in the direction of the arrow 51 on the touch panel of the input equipment 100. Although a case in which driving is controlled by a swipe operation in a direction indicated in each arrow has been explained in the above example, it may be by a flick operation.

As described above, according to the second embodiment, the X-ray generator (for example, the X-ray tube 4, and the like) generates X-rays. The arm 3 holds the X-ray generator at one end. The apparatus main body 9 has wheels (for example, the front wheels 6 and the rear wheels 7). The support column 2 is supported turnably about the axis in the vertical direction, and holds the other side of the arm 3. The input equipment 100 is arranged on the support column 2, and controls driving to a different direction of the apparatus main body 9 by accepting an operation to the upper side or an operation to the lower side in the vertical direction. Therefore, in the mobile X-ray-diagnostic apparatus 1 according to the second embodiment, even when the support column 2 turns, the position to operate, and an operation direction do not change, and it is possible to let an operator grasp the operating direction intuitively, and to improve the operability related to movement.

Third Embodiment

The first and the second embodiments have been explained; however, other than the first and the second embodiments described above, various different forms may be applied.

In the first embodiment, a case in which the input equipment 100 has two operating switches has been explained. However, the embodiment is not limited thereto, and for example, the input equipment 100 may include three or more operating switches. In such a case, three or more operating switches are arranged at positions shifted in a vertical direction.

Furthermore, in the first embodiment, a case in which the input equipment 100 is arranged on one side surface of the support column 2 has been explained. However, the embodiment is riot limited thereto, and for example, the input equipment 100 may be arranged on more than one side surface of the support column 2. In this case, for example, operating switches are arranged at positions shifted in a vertical direction on three side surfaces of the support column 2 except a side surface on which the arm 3 is held.

Figure 9:
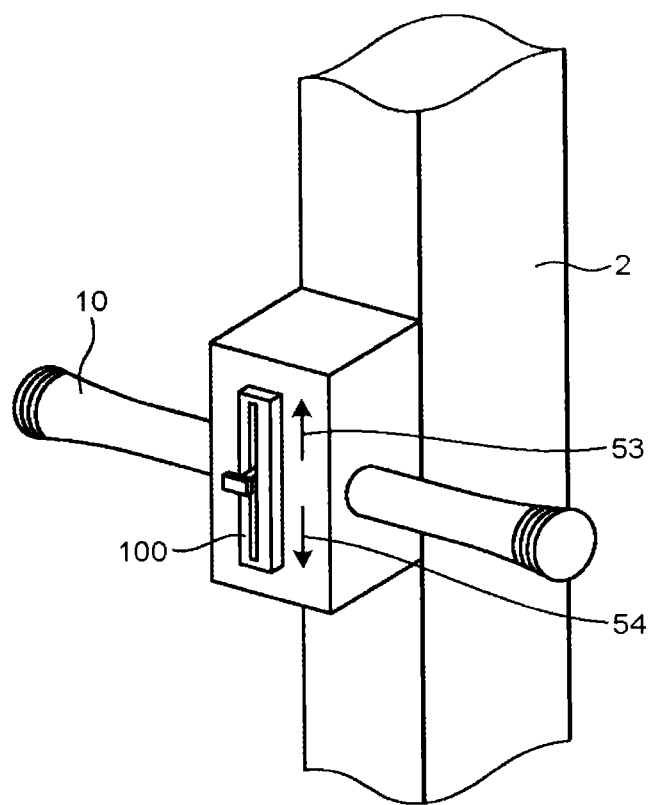
FIG. 9 depicts one example of input equipment according to a third embodiment.

Moreover, in the first and the second embodiments, a case in which driving is operated by the operating switches of the touch panel has been explained. However, the embodiment is not limited thereto, and various kinds of devices can be used as the input equipment. FIG. 9 depicts one example of the input equipment 100 according to a third embodiment. For example, the input equipment 100 controls driving by a slide volume as shown in FIG. 9. For example, the input equipment 100 controls forward movement of the apparatus by accepting a slide operation to an upper side (for example, a direction of an arrow 53 in FIG. 9), and controls forward movement of the apparatus by accepting a slide operation to a lower side (for example, a direction of an arrow 54 in FIG. 9) in the slide volume. That is, the operator drives the apparatus toward the front side by sliding in the direction of the arrow 53, and drives the apparatus toward the rear side by sliding in the direction of the arrow 54 in the slide volume of the input equipment 100.

A driving speed of the apparatus can be controlled according to a how far it is slid. For example, the input equipment 100 controls to stop the apparatus when the slide volume is positioned in center. When the input equipment 100 accepts a slide operation in the direction of the arrow 53, and controls the apparatus to move forward at more speed as it is slid more toward the upper side. On the other hand, the input equipment 100 accepts a slide operation in the direction of the arrow 54, and controls to move the apparatus at more speed as it is slid more toward the lower side.

Furthermore, in the first embodiment, a case in which the operating switch 101 and the operating switch 102 are arranged on a plane of the joining unit parallel to the side surface of the support column 2 has been explained. However, the embodiment is not limited thereto, and for example, the operating switches may be arranged on a plane of the joining unit perpendicular to the side surface of the support column 2. One example is explained using FIG. 7A. For example, the operating switch 101 may be arranged on an upper surface of the joining unit to which the second operating handle 10 is arranged, and the operating switch 102 may be arranged on a lower surface thereof. As described, by arranging multiple operating switches at positions shifted in the vertical direction and on different planes, operating errors can be suppressed.

Furthermore, in the first and the second embodiments, a case in which the input equipment 100 and the second operating handle 10 are arranged on the support column 2 having predetermined length has been explained. However, the embodiment is not limited thereto, and for example, the input equipment 100 and the second operating handle 10 may be arranged on the support column 2 the height of which is adjustable stepwise. As one example, the input equipment 100 and the second operating handle 10 may be arranged on the support column 2 that can be stored according to a condition at moving, at imaging, or the like, and that thus varies in height.

Figure 10:
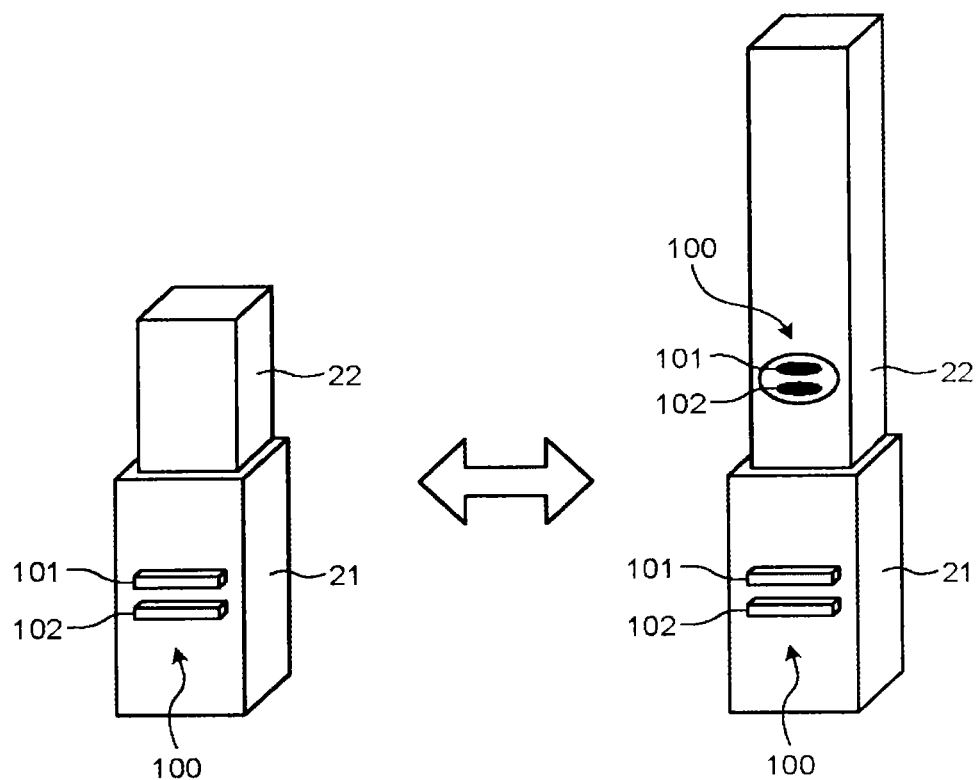
FIG. 10 depicts one example of the input equipment according to the third embodiment.

An example of such an arrangement is explained using FIG. 10. FIG. 10 depicts one example of the input equipment according to the third embodiment. In FIG. 10, a case in which the input equipment 100 is arranged on the support column 2 that varies in height is shown. For example, as shown in FIG. 10, the mobile X-ray-diagnostic apparatus 1 includes a first support column 21 on a base side and a second support column 22 on an end side, and the second support column 22 is stored in the first support column 21. In the mobile X-ray-diagnostic apparatus 1 configured as such, for example, when moving, the second support column 22 is stored inside the first support column 21, and the column is low in height, as shown in a drawing on a left side of FIG. 10. On the other hand, in the mobile X-ray-diagnostic apparatus 1 at imaging, the second support column 22 extends out from the inside of the first support column 21 to the upper side, and the height of the column increases as shown in a drawing on a right side of FIG. 10.

The input equipment 100 is arranged on a side surface of the first support column 21 as shown in FIG. 10, for example. Specifically, the operating switch 101 is arranged on an upper side in the vertical direction in the first support column 21, and the operating switch 102 is arranged on a lower side in the vertical direction in the first support column 21. Moreover, the input equipment 100 may be arranged on the second support column 22 as shown in the drawing on the right side of FIG. 10. In such a case, for example, the operating switch 101 is arranged on an upper side in the vertical direction and the operating switch 102 is arranged on a lower side on a side surface of the second support column 22 that is stored inside the first support column 21, as shown in the drawing on the right side of FIG. 10. If the operating switch 101 and the operating switch 102 are formed in a convex shape, the switches get caught when the second support column 22 is being stored in the first support column 21. Therefore, the operating switch 101 and the operating switch 102 are formed in a concave shape, or are formed so as not to stick out from a side surface of the second support column 22. For example, on a side surface of the second support column 22, a concave portion that is concave toward the center of the second support column 22 is arranged on a side surface of the second support column 22, and at that portion, the operating switch 101 and the operating switch 102 are arranged. Alternatively, the operating switch 101 and the operating switch 102 are arranged so as to be embedded on a side surface of the second support column 22. Note that although only the first support column 21 and the second support column 22 are shown in FIG. 10, the arm 3 is connected to an upper part of the second support column 22 in an actual state. Moreover, although a case in which the second operating handle 10 is not arranged is shown as an example in FIG. 10, the second operating handle 10 may be arranged on the first support column 21.

Furthermore, in the first and the second embodiments described above, a case in which the mobile X-ray-diagnostic apparatus 1 has the support column 2 has been explained as an example, the embodiment is not limited thereto, and for example, it may be applied to the mobile X-ray-diagnostic apparatus 1 that does not have the support column 2.

Figure 11A:
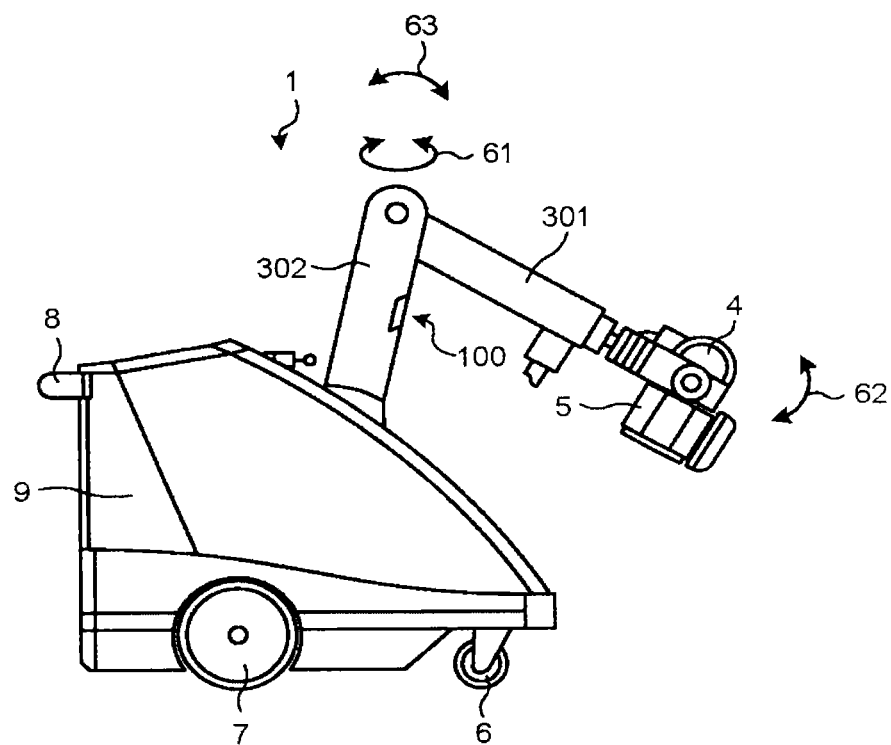
FIG. 11A depicts one example of an entire configuration of a mobile X-ray-diagnostic apparatus according to the third embodiment.

FIG. 11A depicts one example of an entire configuration of the mobile X-ray-diagnostic apparatus 1 according to the third embodiment. In FIG. 11A, components to which the same reference symbols as those in FIG. 1 are given are similar to those in FIG. 1, and duplicated explanation is omitted as appropriate. For example, the mobile X-ray-diagnostic apparatus 1 according to the third embodiment includes a first arm 301 and a second arm 302 as shown in FIG. 11A.

The first arm 301 holds the X-ray generator at one end. Specifically, one end of the first arm 301 is connected to the second arm 302, and the X-ray tube 4 and the X-ray movable collimator 5 are arranged on the other end. The first arm 301 is joined to the second arm 302 to be pivoted about a junction with the second arm 302 such that the X-ray tube 4 and the X-ray movable collimator 5 move vertically. For example, the first arm 301 is joined such that an end portion on an opposite side vertically moves pivoted about an end side joined with the second arm 302, as indicated by an arrow 62 in FIG. 11A.

The second arm 302 is supported turnably about an axis in the vertical direction, and is joined with the first arm 301. Specifically, one end of the second arm 302 is joined with the apparatus main body 9, and the other end is joined with the first arm 301, as shown in FIG. 11A. The second arm 302 is supported turnably about the vertical direction as the rotation axis as indicated by an arrow 61 in FIG. 11A. The second arm 302 is joined with the apparatus main body 9 so as to tilt in a front-back direction of the apparatus main body 9 about a junction with the apparatus main body 9 as the fulcrum. For example, as indicated by an arrow 63 in FIG. 11A, the second arm 302 is joined such that an end portion on an opposite side moves forward and backward about an end side on which the second arm 302 is joined with the apparatus main body 9 as the fulcrum. The second arm 302 has the input equipment 100 on a side surface as shown in FIG. 11A. The second arm 302 may be supported turnably about a direction of length as the rotation axis.

Figure 11B:
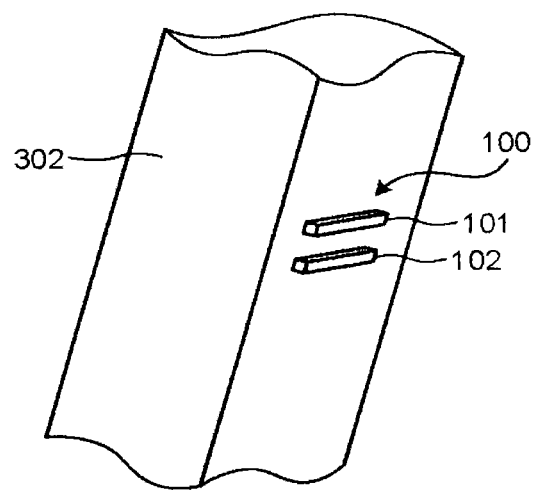
FIG. 11B depicts one example of an input equipment of the mobile X-ray-diagnostic apparatus according to the third embodiment.

FIG. 11B depicts one example of the input equipment 100 of the mobile X-ray-diagnostic apparatus 1 according to the third embodiment. For example, the input equipment 100 is arranged on a side surface of the second arm 302. In the input equipment 100, the operating switch 101 and the operating switch 102 are arranged such that positions in the vertical direction of the second arm 302 differ from each other, as shown in FIG. 11B. For example, as shown in FIG. 11B, the operating switch 101 is arranged on an upper side on the side surface of the second arm 302, and the operating switch 102 is arranged on a lower side on the side surface thereof. As described above, even though the second arm 302 is joined such that the end on the opposite side moves in the front-back direction about the end side joined with the apparatus main body 9 as the fulcrum, the vertical positional relation of the operating switch 101 and the operating switch 102 is not inversed. Therefore, if when the operating switch 101 and the operating switch 102 are arranged on the second arm 302, the operability in movement can be improved.

Figure 12:
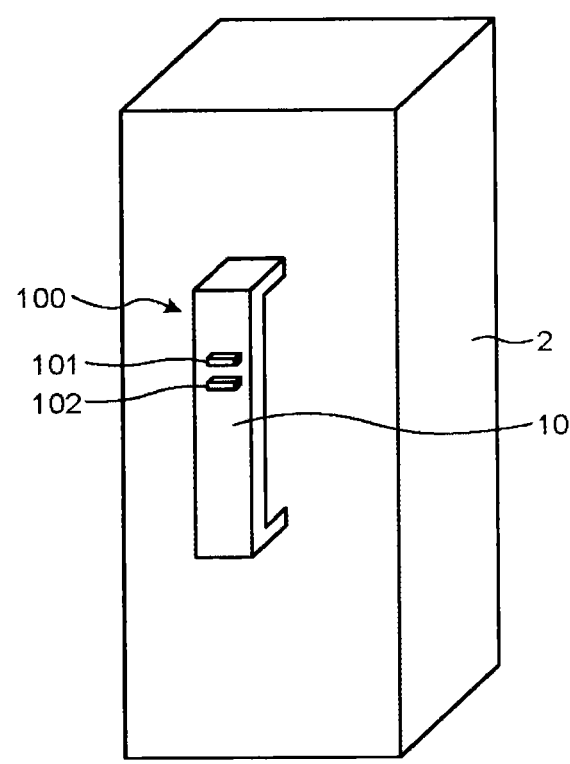
FIG. 12 depicts one example of the input equipment according to the third embodiment.

Moreover, in the first and the second embodiments described above, a case in which the input equipment 100 (for example the operating switch 101 and the operating switch 102) is arranged at the joint with the support column 2, on the side surface of the support column 2, or on the side surface of the second arm 302 has been explained as an example. However, the embodiment is not limited thereto, and for example, the input equipment 100 may be arranged at the second operating handle 10. FIG. 12 depicts one example of the input equipment according to the third embodiment. For example, as shown in FIG. 12, the second operating handle 10 is arranged on a side surface of the support column 2 such that a longitudinal direction of a holding portion is parallel to the vertical direction. The operating switch 101 and the operating switch 102 are arranged vertically at the holding portion of the second operating handle 10 along the longitudinal direction. Specifically, the operating switch 101 and the operating switch 102 are arranged on the second operating handle 10 at different positions in the vertical direction. For example, the operating switch 101 is arrange on an upper side in the vertical direction, and the operating switch 102 is arranged on a lower side in the vertical direction as shown in FIG. 12. This enables easy operation with one hand, and easy grasp of relation between the operating switches and the driving directions, thereby improving the operability in movement.

In FIG. 10 to FIG. 12 described above, a case in which the input equipment 100 corresponds to the operating switch 101 and the operating switch 102 has been explained as an example. However, the embodiment is not limited thereto, and the input equipment 100 indicated in FIG. 10 to FIG. 12 may be a touch panel, a button, a seesaw switch, or a slide volume explained in the first or the second embodiment.

Furthermore, in the first and the second embodiments described above, a case in which the second operating handle 10 is fixed at a predetermined height on the support column 2 has been explained as an example. However, the embodiment is not limited thereto, and for example, it may be arranged such that the heights of the input equipment 100 and the second operating handle 10 on the support column 2 may be arbitrarily changed.

Moreover, in the first and the second embodiments, the explained configurations are only examples, and the mobile X-ray-diagnostic apparatus 1 according to the present application can have various configurations. For example, the apparatus main body 9, the X-ray tube 4, the X-ray movable collimator 5, and the like shown in FIG. 1 may be in arbitrary shapes. Furthermore, arrangement of the components explained as ones provided in the apparatus main body 9 can be arbitrarily changed. For example, the high voltage generator that has been explained to be provided in the apparatus main body 9 may be arranged inside a box including the X-ray tube 4.

As explained above, according to the first, the second, and the third embodiments, the mobile X-ray-diagnostic apparatus of the embodiments enables to improve the operability in movement.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A mobile X-ray-diagnostic apparatus comprising:
an X-ray generator configured to generate X-rays;
an arm configured to hold the X-ray generator at one end;
a main body configured to include wheels to move the mobile X-ray diagnostic apparatus;
a support column is turnably supported on the main body about a vertical direction as an axis, and configured to support another end of the arm; and
at least two input equipment are arranged on the support column such that heights in the vertical direction differ from each other, wherein a rotation of the wheels is controlled by an input operation to the at least two input equipment, and
different functions relating to the rotation of the wheels are assigned to the at least two input equipment, respectively.

2. The mobile X-ray-diagnostic apparatus according to claim 1, wherein at least two switches are arranged such that distances from a floor are invariable irrespective of a turned state of the support column, as the at least two input equipment.

3. The mobile X-ray-diagnostic apparatus according to claim 1, wherein at least two switches are arranged along a rotation axis of the support column, as the at least two input equipment.

4. The mobile X-ray-diagnostic apparatus according to claim 1, further comprising
an operating handle to control the wheels that is arranged in the main body at a position opposing to the support column.

5. The mobile X-ray-diagnostic apparatus according to claim 1, wherein the at least two input equipment is arranged on a side surface of the support column that is substantially perpendicular to a floor.

6. The mobile X-ray-diagnostic apparatus according to claim 1, further comprising
a grip is included in the support column, is held by an operator, and is arranged near the at least two input equipment.

7. The mobile X-ray-diagnostic apparatus according to claim 1, further comprising
a grip is included in the support column, is held by an operator, and on which the at least two input equipment is provided.

8. The mobile X-ray-diagnostic apparatus according to claim 1, wherein
the support column extends from the main body in the vertical direction,
the arm configured to hold the X-ray generator extends from the support column in a second direction that is different from the vertical direction, and turning the support column around the axis about which the support column is turnably supported changes an orientation of the second direction, at which the arm extends from the support column, with respect to a primary axis of the main body, and
the rotation of the wheels causes the main body to move in a direction orthogonal to the vertical direction.

9. A mobile X-ray-diagnostic apparatus comprising:
an X-ray generator configured to generate X-rays;
an arm configured to hold the X-ray generator at one end;
a main body configured to include wheels to move the mobile X-ray diagnostic apparatus;
a support column is turnably supported on the main body about a vertical direction as an axis, and configured to support another end of the arm; and
input equipment is arranged on the support column, wherein
rotational directions of the wheels are controlled by an operation toward an upper side and an operation toward a lower side to the input equipment, and
different rotational directions of the wheels are assigned to the operation toward the upper side and the operation toward the lower side, respectively.

10. A mobile X-ray-diagnostic apparatus comprising:
an X-ray generator configured to generate X-rays;
a first arm configured to hold the X-ray generator at one end;

a main body configured to include wheels to move the mobile X-ray diagnostic apparatus;

a second arm is turnably supported on the main body about any one of a vertical direction and a longitudinal direction as an axis, and configured to support another end of the first arm; and at least two input equipment are arranged on the second arm such that heights in the vertical direction differ from each other, wherein a rotation of the wheels is controlled by an input operation to the at least two input equipment, and different functions relating to the rotation of the wheels are assigned to the at least two input equipment, respectively.

11. The mobile X-ray-diagnostic apparatus according to claim 10, wherein at least two switches are arranged such that vertical positional relation is invariable irrespective of a turned state of the second arm, as the at least two input equipment.

12. The mobile X-ray-diagnostic apparatus according to claim 10, further comprising an operating handle to control the wheels that are arranged in the main body at a position opposing to the second arm.

13. The mobile X-ray-diagnostic apparatus according to claim 10, further comprising a grip is included in the second arm, is held by an operator, and on which the at least two input equipment is provided.

* * * * *